US00PP19803P2

(12) United States Plant Patent
Radler

(10) Patent No.: US PP19,803 P2
(45) Date of Patent: Mar. 10, 2009

(54) SHRUB ROSE PLANT NAMED 'RADRAL'

(50) Latin Name: *Rosa hybrida*
Varietal Denomination: Radral

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/980,538

(22) Filed: Oct. 31, 2007

(51) Int. Cl.
*A01H 5/00* (2006.01)

(52) U.S. Cl. ..... Plt./106; Plt./105
(58) Field of Classification Search ..... Plt./106, Plt./105
See application file for complete search history.

(56) References Cited

U.S. PATENT DOCUMENTS

PP17,346 P2 * 1/2007 Radler
PP19,032 P2 * 7/2008 Radler

OTHER PUBLICATIONS

'RADral'available at http://www.helpmefind.com/rose/pl-.php?n=49291.*

* cited by examiner

*Primary Examiner*—Wendy C Haas
(74) *Attorney, Agent, or Firm*—Buchanan Ingersoll & Rooney PC

(57) ABSTRACT

A new and distinct variety of rose plant is provided which forms in abundance on a substantially continuous basis attractive double cuplike blossoms that are orange and finish to light coral-salmon coloration. The vegetation is vigorous and the growth habit is rounded and fairly loose. Attractive ornamental green foliage having a glossy appearance is formed which tends to be bronze-red when immature. The resistance to secondary leafspot and powdery mildew has been excellent during observations to date. The hardiness of the new variety also is excellent. The new variety is particularly well suited for growing as distinctive ornamentation in parks, gardens, and residential settings.

1 Drawing Sheet

Figure 1:
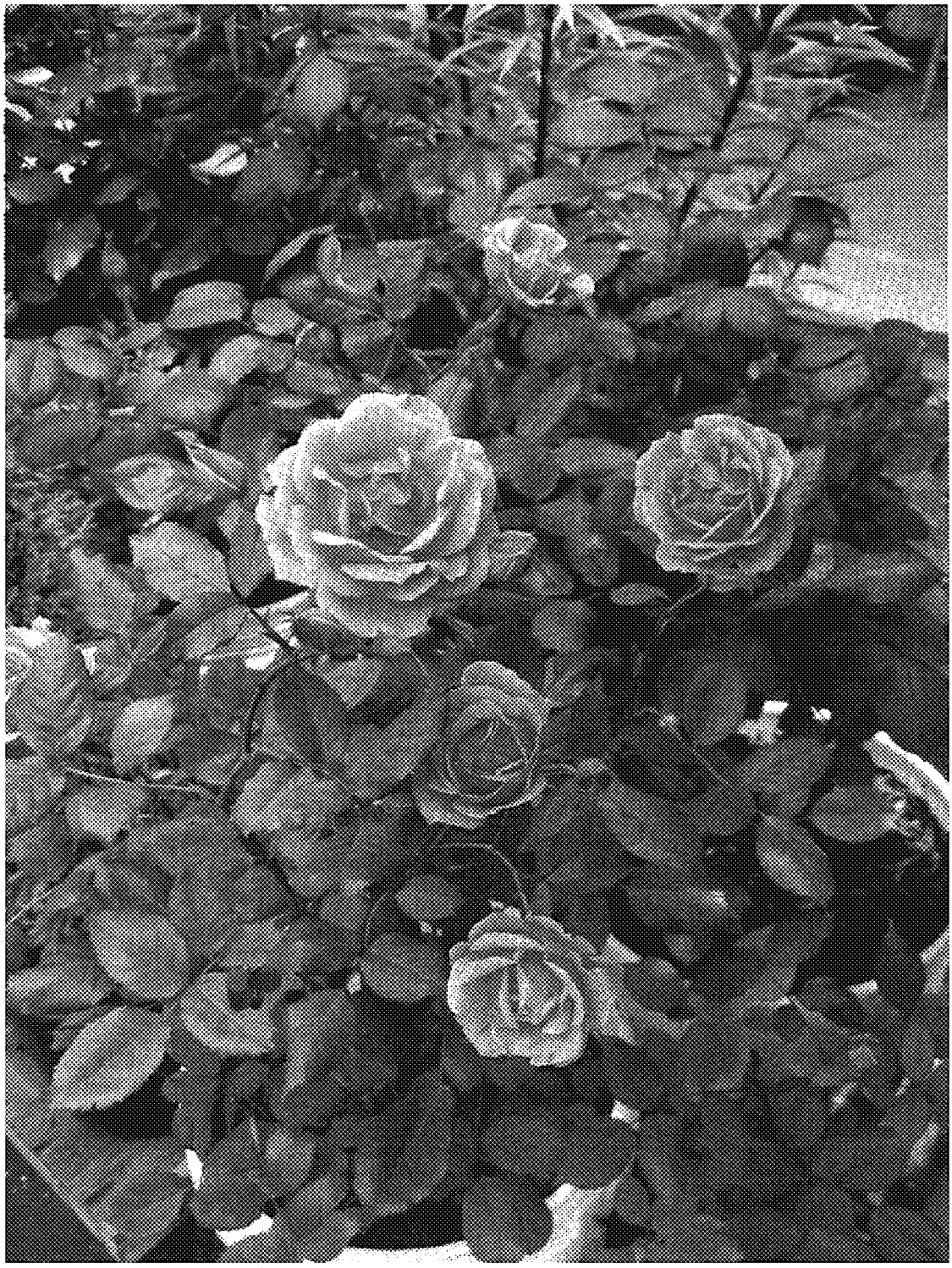

Botanical/commercial classification: *Rosa hybrida*/Shrub Rose Plant.
Varietal denomination: cv. Radral.

Summary of the Invention

The new variety of *Rosa hybrida* shrub rose plant of the present invention was created at Greenfield, Wisc. U.S.A., by artificial pollination wherein two parents were crossed which previously had been studied in the hope that they would contribute the desired characteristics. The female parent (i.e., the seed parent) was the 'Radorg' variety (non-patented in the United States). The male parent (i.e., the pollen parent) of the new variety was the 'Rader' variety (non-patented in the United States). The parentage of the new variety can be summarized as follows:

'Radorg' ×'Rader'.

The seeds resulting from the above pollination were sown and small plants were obtained which were physically and biologically different from each other. Selective study resulted in the identification of a single plant of the new variety.

It was found that the new shrub rose plant of the present invention possesses the following combination of characteristics:

(a) abundantly and substantially continuously forms attractive double cuplike blossoms that are orange and finish to light coral-salmon coloration, (b) exhibits a rounded and fairly loose growth habit,
(c) forms vigorous vegetation,
(d) abundantly forms attractive ornamental green foliage with a glossy appearance that is bronze-red when immature,
(e) exhibits excellent resistance to secondary leafspot and powdery mildew, and
(f) exhibits excellent cold hardiness.

The new variety displays a good repeat blooming character. The growth habit is very vigorous and the canes commonly are of medium to heavy caliper.

The new variety well meets the needs of the horticultural industry. It can be grown to advantage as an attractive shrub rose plant in parks, gardens, public areas, and in residential settings. The new variety is particularly well suited for providing attractive ornamentation in the landscape. The orange blossoms contrast nicely with the glossy green foliage.

The new variety of the present invention can be readily distinguished from its ancestors. Unlike the new variety the 'Radorg' variety displays a more uniform growth habit and forms smaller blossoms. Also, the 'Radorg' variety tends to form less colorful young foliage and is less resistant to secondary leafspot and powdery mildew. The 'Rader' variety forms dissimilar red blossoms having more petals and tends to form less colorful young foliage.

The characteristics of the new variety have been found at Wasco, Calif., U.S.A., and elsewhere, to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radral' and is being marketed under the CAREFREE CELEBRATION trademark.

Brief Description of the Photograph

The accompanying photograph shows, as nearly true as it is reasonably possible to make the same in a color illustration of this character, a typical specimen of the new variety. A mature flowering plant is shown during the summer while growing in a container at Greenfield, Wisc. U.S.A. The attractive orange blossoms and glossy foliage are displayed.

Detailed Description

The chart used in the identification of colors is that of the Royal Horticultural Society (R.H.S. Colour Chart), London, England. The description is based on the observation of three-year-old specimens of the new variety during September while growing outdoors on their own roots near West Grove, Pa., U.S.A.

Class: Landscape Shrub Rose.

Plant:

*Height.*—Approximately 4 to 5 feet on average at the end of the growing season, and commonly assumes a mature height of approximately 5.5 feet.

*Width.*—Approximately 5.5 feet on average at the end of one growing season, and commonly continues to display approximately the same width at full maturity.

*Habit.*—Rounded and fairly loose.

Branches:

*Color.*—Young stems: commonly between Greyed-Orange Group 175A and Yellow-Green Group 146C. Adult wood: primarily Greyed-Orange Group 175A with some Green Group 137D.

*Texture.*—Young stems: smooth. Adult wood: smooth.

*Caliper.*—Canes are medium to heavy caliper.

*Thorns.*—On young stems: commonly bear several thorns averaging between 0.5 to 5 mm in length, and near Greyed-Red Group 182A in coloration. On mature wood: commonly bear large as well as small prickles that are Greyed-Red Group 182A in coloration.

Leaves:

*Leaflet number.*—3, 5, and 7.

*Leaflet texture.*—With a glossy finish.

*Leaflet size.*—Commonly approximately 4 to 5 cm in length on average, and approximately 3 to 4 cm in width on average at the widest point.

*Leaflet shape.*—Oval to somewhat ovate with acute to somewhat acuminate apices, and rounded bases.

*Leaflet margins.*—Serrulate.

*Leaf size.*—Commonly approximately 9.5 to 14.5 cm in length on average, and approximately 10.5 cm in width on average at the widest point.

*Overall appearance.*—Very abundant, and medium green with a glossy finish.

Color. —Young leaves: upper surfaces commonly are between Green Group 139A and Yellow-Green Group 147A and lightly suffused with near Greyed-Purple Group 183B and Greyed-Purple Group 187C, and under surfaces commonly are between Green Group 139C and Yellow-Green Group 147B and moderately suffused with near Greyed-Purple Group 183B and Greyed-Purple Group 187C. Mature leaves: upper surfaces commonly are between Green Group 139A and Yellow-Green Group 147A, and under surfaces commonly are between Yellow-Green Group 147B and 147C.

*Stipules.*—Configuration: commonly possess moderately narrow medium to long points that turn out of an angle of more than 45 degrees. Length: commonly approximately 2 to 2.5 cm. Width: commonly approximately 0.8 cm at the widest portion of the body. Coloration: near Green Group 138A.

*Petiole.*—Length: commonly approximately 3.7 cm on average. Diameter: commonly approximately 2 mm on average. Texture: slightly bristling. Color: Green Group 138A.

*Rachis.*—Average in caliper, the upper surface commonly is moderately grooved with some stipitate glands and tiny hairs on the edges of the grooves, and the underside commonly is somewhat rough with a few stipitate glands and numerous small prickles.

Inflorescence:

*Peduncle.*—Bearing: typically erect and very strong. Diameter: commonly Approximately 3 mm. Texture: smooth with some stipitate glands and a few hairs. color: commonly between Yellow-Green Group 144B and 144C, and sometimes moderately suffused with between Greyed-Purple Group 183B and 183C.

*Sepals.*—Length: commonly approximately 2.5 cm on average. Width: commonly approximately 1 cm on average. Extensions: commonly absent. Texture: the inner surface is lined and edged with very fine wooly tomentum, and the margins commonly are lined with a few stipitate glands and hairs. Apex: acute. Color: commonly near Yellow-Green Group 144A fading to Yellow-Green Group 144C. Number: five.

*Buds.*—Shape: commonly very pointed to urn-shaped as the calyx breaks. Length: as the calyx breaks commonly approximately 2 to 2.5 cm on average. Diameter as the calyx breaks commonly approximately 2 to 2.5 cm at the widest point. Texture: commonly bears numerous stipitate glands and some hairs. Color (as the calyx breaks): commonly between Yellow-Green Group 144A and 144B and often moderately suffused with Greyed-Purple Group 183B and 183C.

*Flower.*—Form: semi-double and cup-shaped. Configuration: when partially opened high-centered with the petals being somewhat loosely spiraled and the petal edges being somewhat slightly reflexed outwards, and when fully opened cup-shaped to somewhat flat and the petal edges being flat to undulated and very slightly reflexed outward, with the inner petals being crinkled/ruffled. Diameter: commonly approximately 8.5 to 9 cm on average when fully open. Bearing: commonly in clusters of up to approximately 5 blooms per cluster, with the clusters being irregularly rounded and borne on medium to long stems having lengths of approximately 20 to 30 cm. Color (when opening begins): upper surface: near Red Group 38A and Red Group 39B, and at the base near Yellow-Orange Group 14B. Under surface: near Red Group 43C and 43D, and at the base near Yellow Group 13C. Color (when blooming): upper surface: near Red Group 48C, near the base Orange Group 29B, and at the point of attachment Yellow Group 13C. Under surface: near Red Group 39B, near the base Orange-Red Group 32C, and at the point of attachment Yellow Group 13C. Color (at end of blooming) upper surface: near Red Group 49B, and near the base Yellow-Orange Group 14D. Under surface: near Red Group 51C, and near the base Yellow Group 13D. Lastingness: commonly approximately 4 or 5 days or more on the plant depending upon environmental conditions, and approximately 4 to 5 days when cut and placed in a vase. Fragrance: strong citrus-rose. Petal form: substantially round to very broadly obovate. Petal number: commonly approximately 13 to 14 on average. Petal apex: commonly rounded and sometimes notched with one or two notches. Petal size: commonly approximately 3.5 cm in length on average and approximately 3 cm in width on average. Petal texture: medium to thick in substance, the upper surfaces commonly are moderately velvety to satiny in appearance, and the under surfaces are mostly satiny to somewhat satiny. Petaloid number: commonly approximately 1 to 2 on average per flower and arranged irregularly. Petaloid length: commonly approximately 3.4 cm on average. Petaloid width: commonly approximately 1.1 cm at the widest point. Petal drop: very good, the petals commonly drop cleanly and freely. Stamen number: approximately 165 to 170 on average arranged regularly about the pistils. Anthers: approximately 1 mm in size. Anther color: commonly between Greyed-Orange Group 167D and Greyed-Orange Group 168C when immature, and Greyed-Orange Group 165A when mature. Filament length: commonly approximately 7 to 12 mm, and most bear anthers. Filament color Greyed-Orange Group 169C with Yellow-Orange Group 17C at the base. Pollen: commonly is present in a moderate to abundant quantity and commonly is near Yellow Group 13B in coloration. Pistils: separate and free, and commonly approximately 40 on average. Stigma color: commonly between Yellow Group 8D and Yellow Group 9D. Styles: moderately uneven in length, commonly approximately 4.5 mm in length, and approximately 0.25 mm in diameter. Style color commonly near Yellow Group 8D suffused with Red Group 46D.

*Receptacle.*—Configuration: ovoid. Size: commonly approximately 7 mm in diameter on average. Texture: commonly somewhat bristly on surface. Color: near Yellow-Green Group 146D.

Development:

*Vegetation.*—Vigorous.

*Blossoming.*—Very abundant and substantially continuous during the growing season.

Resistance to diseases. —Excellent with respect to secondary leafspot and powdery mildew, when compared to commercial rose varieties being grown under comparable conditions near West Grove, Pa., U.S.A.

*Resistance to insects.*—Excellent with respect to rose midge.

Cold hardiness. —Excellent, and has proven to be completely winter hardy in U.S.D.A. Hardiness Zone No. 5.

The new 'Radral' variety has not been observed under all possible environmental conditions to date. Accordingly, it is possible that the phenotypic expression may vary somewhat with changes in light intensity and duration, cultural practices, and other environmental conditions.

I claim:

1. A new and distinct shrub rose plant characterized by the following combination of characteristics:

(a) abundantly and substantially continuously forms attractive double cuplike blossoms that are orange and finish to light coral-salmon coloration, (b) exhibits a rounded and fairly loose growth habit, (c) forms vigorous vegetation, (d) abundantly forms attractive ornamental green foliage with a glossy appearance that is bronze-red when immature, (e) exhibits excellent resistance to secondary leafspot and powdery mildew, and (f) exhibits excellent cold hardiness;

substantially as herein shown and described.

* * * * *